United States Patent [19]

Kim et al.

[11] Patent Number: 5,091,381

[45] Date of Patent: Feb. 25, 1992

[54] 2H-1,3,4-BENZOTRIAZEPIN-2-ONES

[75] Inventors: Sun H. Kim, Chestnut Hill; John E. Taylor, Upton, both of Mass.

[73] Assignee: Biomeasure, Inc., Hopkinton, Mass.

[21] Appl. No.: 684,715

[22] Filed: Apr. 12, 1991

[51] Int. Cl.$^5$ .................... C07D 255/04; A61K 31/55
[52] U.S. Cl. .................................... 514/183; 540/501
[58] Field of Search ........................ 514/183; 540/501

[56] References Cited
PUBLICATIONS

Max Busch "Berichte", vol. 27, pp. 2897-2904 (1894).

Primary Examiner—Robert T. Bond
Attorney, Agent, or Firm—Fish & Richardson

[57] ABSTRACT

Peripheral benzodiazepines (BZDs) are useful in treating disorders caused by abnormal level of peripheral benzodiazepene receptor activity and having, in one aspect, the formula:

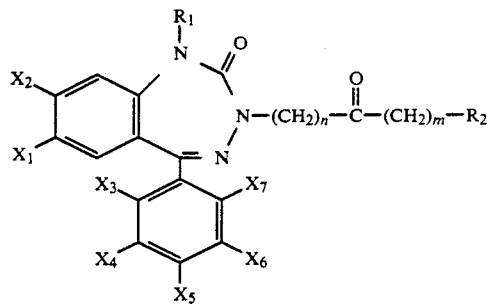

(I)

wherein each X, $X_1$, $X_2$, $X_3$, $X_4$, $X_5$, $X_6$, and $X_8$, independently, is hydrogen, halogen (F, Cl, Br, I), $C_1$-$C_4$ straight or branched alkyl, $C_1$-$C_4$ alkoxy, $C_1$-$C_4$ alkylthio, hydroxy, nitro, cyano, amino, or trifluoromethyl; $R_1$=H, $C_1$-$C_4$ alkyl, cyclo $C_3$-$C_5$ alkyl, $C_1$-$C_4$ alkenyl, $CH_2$—$CO_2H$, or $CH_3$—C=O; $R_2$=a member of the group of the formula (Ia)

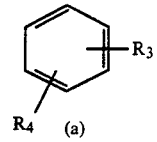

(a)

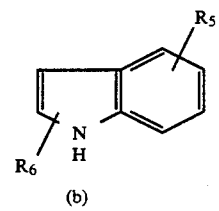

(b)

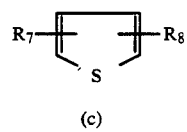

(c)

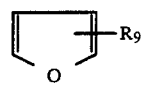

(d)

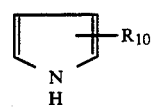

(e)

wherein each $R_3$, $R_4$, $R_8$, $R_9$, $R_{10}$ and $R_{11}$, independently, can be any of the groups listed as possibilities for $X_1$-$X_8$, and can be attached at any available ring carbon atom, said $R_2$ group being bonded to ($CH_2$) in via any available ring carbon atom; n=0 or 1; and m=an integer between 1 and 4 provided that m is at least 1 when n=0.

20 Claims, 2 Drawing Sheets

BIM-18154

BIM-18272

FIG. 1

BIM-18156

BIM-18268

BIM-18269

FIG. 2

2H-1,3,4-BENZOTRIAZEPIN-2-ONES

BACKGROUND OF THE INVENTION

This invention relates to peripheral benzodiazepines.

Based on their predominant receptor binding affinity, benzodiazepines (BZDs) have been grouped into two pharmacologically distinct subclasses: central and peripheral.

Most of the clinically potent benzodiazepines, such as diazepam, oxazepam and clonazepam, have a strong binding affinity to the central BZD receptor, but very weak binding affinity to the peripheral BZD (pBZD) receptor. Central-type receptors are located in the brain and are believed to be involved in the therapeutic action of the central acting BZDs.

Peripheral BZD receptors, on the other hand, are widely distributed in many tissues and cell types including kidney, lung, heart, adrenal cortex, platelets, mast cells, lymphocytes and brain and may be involved in the regulation of cell proliferation and growth. Peripheral benzodiaze pines exhibit "in vivo" immunosuppressive properties by inhibiting the capacity of macrophage to produce lymphokines such as IL-1, IL-6 and TNF (Zavala et al., The J. of Pharmacology and Experimental Therapeutics, 255, 442, 1990). (Johnson, et al., J. Pharmacol. Exp. Therap. 238, 855-859, 1986; Morgan, et al., Proc. Natl. Acad. Sci. U.S.A., 82, 5223-5226, 1985; Solowey, et al., J. Interferon Res. 10, 269-280, 1990 and Cancer Lett., 49, 115, 1990.

SUMMARY OF THE INVENTION

The invention features, in one aspect, a new class of peripheral BZDs having the general formula I:

wherein each X, $X_1$, $X_2$, $X_3$, $X_4$, $X_5$, $X_6$, and $X_7$, independently, is hydrogen, halogen (F, Cl, Br, I), $C_1$-$C_4$ straight or branched alkyl, $C_1$-$C_4$ alkoxy, $C_1$-$C_4$ alkylthio, hydroxy, nitro, cyano, amino, or trifluoromethyl; $R_1$=H, $C_1$-$C_4$ alkyl, cyclo $C_3$-$C_5$ alkyl, $C_1$-$C_4$ alkenyl, $CH_2$—$CO_2H$, or $CH_3$—C=O; $R_2$=a member of the group of the formula (Ia)

(a)

(b)

(c)

(d)

(e)

wherein each $R_3$, $R_4$, $R_7$, $R_8$, $R_9$ and $R_{10}$ independently, can be any of the groups listed as possibilities for $X_1$-$X_7$; and can be attached at any available ring carbon atom, said $R_2$ group being bonded to ($CH_2$) in via any available ring carbon atom; n=0 or 1; and m=an integer between 0 and 4 provided that m is at least 1 when n=0.

In another aspect, the invention features a glass of peripheral BZDs having the general formula II:

wherein $R_1$, $R_2$, and $X_1$, $X_7$ are defined the same as in formula (I).

In one preferred embodiment of the formula (I): $R_1$ is methyl, $X_1$-$X_7$ are hydrogen, $R_2$ is phenyl or substituted phenyl (e.g., 4-chloro, 3,4-dichloro, 2-fluoro or 4-fluoro), and n and m are zero. Preferred compounds include: 1,3-dihydro-5-phenyl-3-(3,4-difluorobenzoyl)-1-methyl-2H-1,3,4-benzotriazepine-2-one, 1,3-dihydro-5-phenyl-3-(4-fluorobenzoyl)-1-methyl-2H-1,3,4-benzotriazepine-2-one, 1,3-dihydro-5-phenyl-3-(3,4-dichlorobenzoyl)-1-methyl-2H-1, 3,4-benzotriazepine-2-one, 1,3-dihydro-5-phenyl-3-(4-chlorobenzoyl)-1-methyl-2H-1,3,4-benzotriazepine-2-one.

In one preferred embodiment of the formula(II), $R_1$; is methyl, $X_1$-$X_7$ are hydrogen, and $R_2$ is phenyl or substituted phenyl (e.g., 4-chloro, 3,4-dichloro, 2-fluoro, 4-fluoro, or 3,4 difluoro). Preferred compounds include: 1,3-dihydro-5-phenyl-3-(4-fluorophenyl)-methyl-1-methyl-2H-1,3,4-benzotriazepin-2-one, 1,3-dihydro-5-phenyl-3-(3,4-dichloro-phenyl)-methyl-1-methyl-2H-1,3,4-benzotriazepin-2-one, 1,3-dihydro-5-phenyl-3-(4-chlorophenyl)-methyl-1-methyl-2H-1,3,4-benzotriazepin-2-one.

In other preferred embodiments, a therapeutically effective amount of the compound and a pharmaceutically acceptable carrier substance, e.g., magnesium carbonate or lactose, form a therapeutic composition, e.g., pill, tablet, capsule or liquid for oral administration to a patient; a liquid or an ointment capable of being administered transdermally, nasally, rectally or sublingualy; a liquid capable of being administered intravenously, parenterally, subcutaneously or intraperitoneally, or an oral or parenteral sustained release formulation.

It is noted that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

Of course, as it will be suggested to one of ordinary skill in the art, the pharmaceutically acceptable salts of the compounds of the invention include the conventional non-toxic salts or the quaternary ammonium salts of the compounds, which are formed for example, from the inorganic acids, such as hydrochloric, hydrobromic, sulfuric and phosphoric acid or from the organic acids such as acetic, propionic, succinic, lactic, malic, tartaric, uric, ascorbic, pamoic, maleic acid and the like.

The compounds of the invention are useful in treating disorder caused by abnormal levels of peripheral benzodiazepine receptor activity, such as found in glioma, melanoma and other cancers and antioimmune disease (Rheumatoid arthrities by modulation or suppression of macrophages lymyphokine secretion).

Other features and advantages will be apparent from the following description of the preferred embodiments of the invention, and from the claims.

DESCRIPTION OF THE PREFERRED EMBODIMENTS

The drawings are first described.

Synthesis

Figure 1:
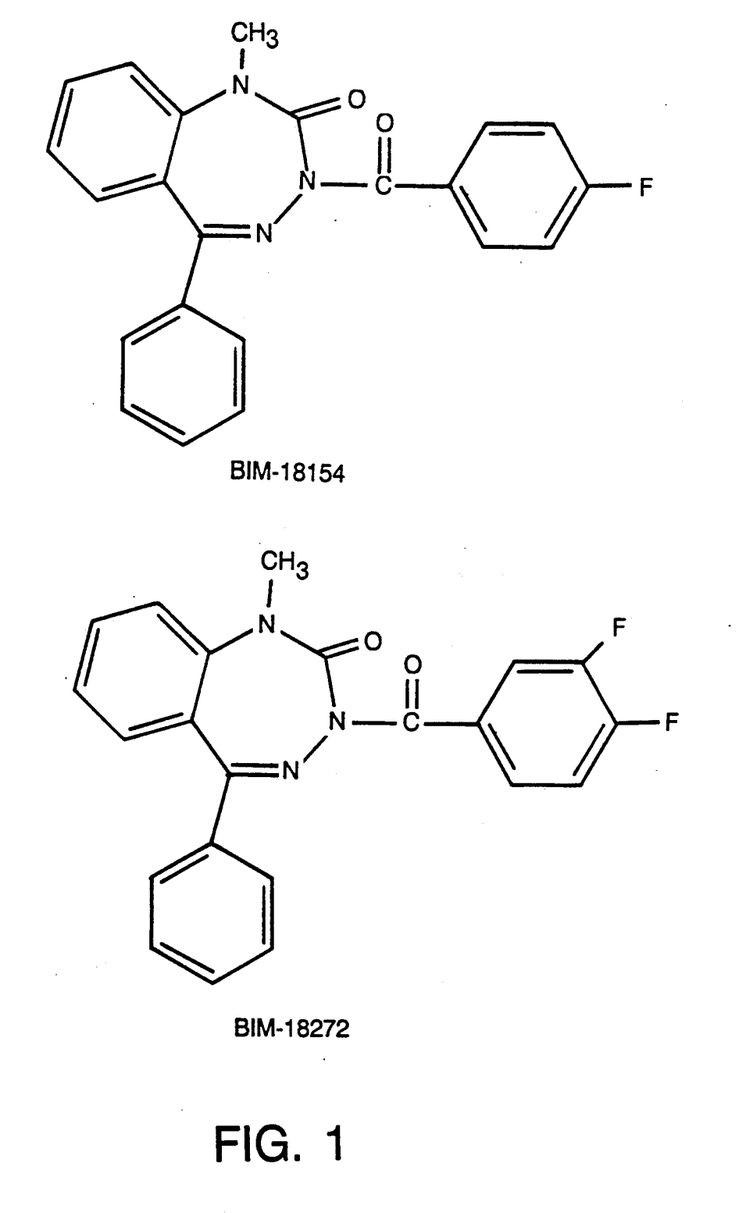
FIGS. 1 and 2 are the structures of three compounds of the invention.
Figure 2:
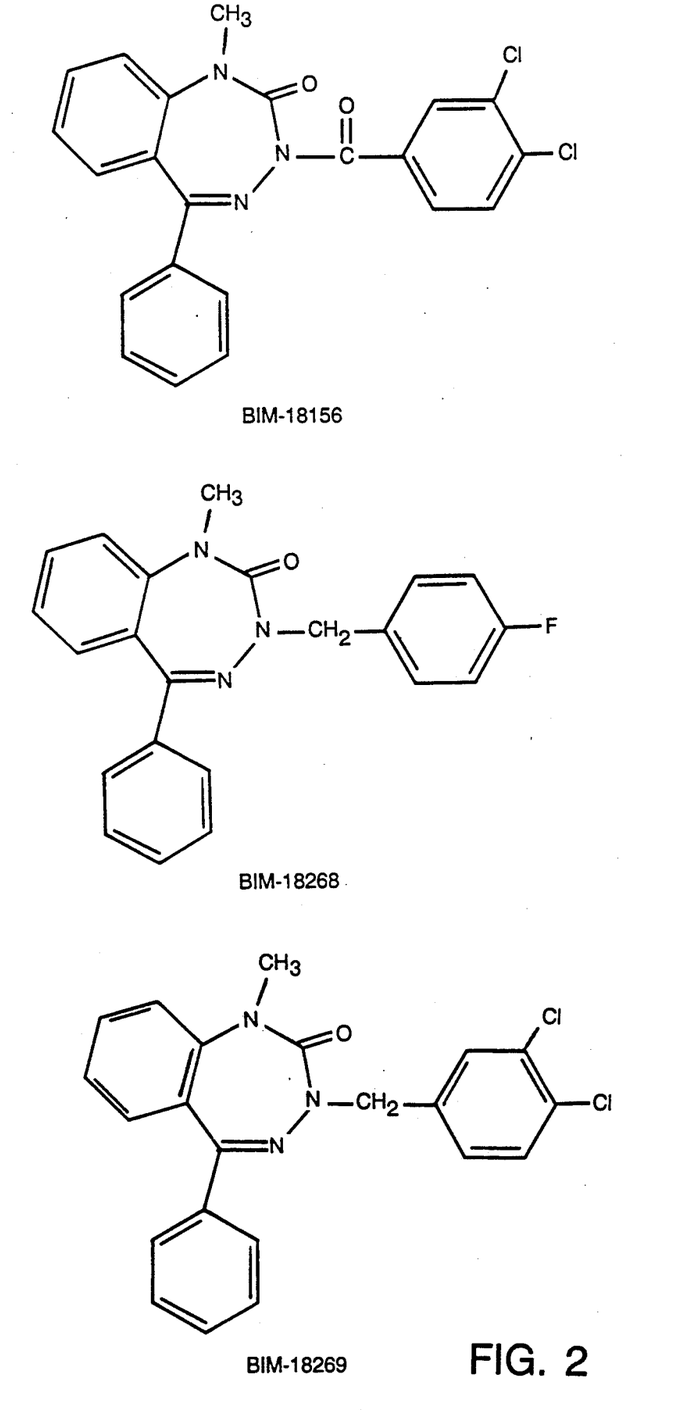

Compounds of the formula (I) and (II) are prepared generally according to the following scheme.

2) X.C.R$_2$ (with C=O)

3) X.C.(CH$_2$)$_m$.R$_2$ (with C=O)

4) X.(CH$_2$)$_n$.R$_2$

5) X—CH$_2$—C—R$_2$ (with C=O)

The intermediates (V) are prepared from the commercially available intermediates (III) and ethylcarbazide at elevated (about 200°–210° C.) temperature [J. Med. Chem. 7, 3S6 (1964)] or from the corresponding hydrazones at elevated temperatures (JP 45,01, 1,148). Compounds of the formula (I) and (II) are prepared by conventional methods and the reaction temperature is maintained below room temperature (e.g., 0° C. to room temperature). The reactions are preferably carried out in an inert organic solvent, e.g., dimethylformamide, tetrahydrofuran, benzene, dimethylsulfoxide and the like. Suitable bases include sodium hydride and sodium alkoxide (e.g., sodium methoxide, sodium ethoxide, sodium 5-butoxide), dimethylsodium and the like.

The intermediates and final products are isolated and purified by standard methods, e.g., column chromatography, crystallization, etc. Purity of the compound is determined by chromatographic, spectroscopic or chemical analysis and the like.

Specific compounds are made as follows.

1,3-Dihydro-5-phenyl-1-methyl-2H-,3,4-benzotriazeoine-2-one

2-N-methylaminobenzophenone (300 mg) and ethylcarbazide (300 mg) are heated at about 200°–210° C. (bath) for about 1 hour and then cooled to room temperature (about 22°–24° C.). Pale yellow residue is triturated with ethanol and pale yellow solid is filtered off. The filtrate is concentrated in vacuo to a dryness and the residue is chromatographed on silica gel (25 g) using Chloroform/acetone (19:1) as eluants. Fractions containing the compound are pooled and the solvents removed in vacuo to a dryness. The final product has an appearance of pale yellow foam (160 mg). TLC: (Silica gel - Chloroform/acetone=9:1, Rf=0.55).

3-(4-Flurobenzoyl)-1-methyl-5-phenyl-2H-1,3,4-benzotriazepine-2-one

To a suspension of NaH (70 mg of NaH was washed with hexane several times dispersed in 50% mineral oil) in 4ml of DNF is added a solution of 1,3-dihydro-5-phenyl-1-methyl-2H-1,3,4-benzotriazepine-2-one (251 mg) in 5 ml DMP under nitrogen atmosphere. After gas evolution ceased, 0.13 ml 4-fluorobenzoyl chloride is added and the mixture is stirred at room temperature overnight (about 12–6 hours). Solvent is removed in vacuo to a dryness and the residue is partitioned between ethylacetate and water. Organic layer is washed with aq.NaHCO$_3$, water, then dried over MgSO$_4$. After evaporation of solvent, the residue is recrystallized using methanol as a solvent. About 97mg of a product is obtained. TLC: (Silica gel - Chloroform/acetone=9:1, Rf.=0.52).

(4-Flurophenyl)methyl-1-methyl-2H-1,3,4-benzotrizepine-2-one

To a suspension of NaH (60 mg of NaH dispensed in 50% mineral oil was washed with hexane several times) in 4 ml DMF is added a solution of 1,3-dihydro-5-phenyl-1-methyl-2H-1,3,4-benzotriazepine-2-one (150 mg) in 4 ml DMF under nitrogen atmosphere. After gas evolution ceased, 0.19 ml of 4-flurobenzyl bromide is added and the mixture is stirred at room temperature for 2 hrs. Solvent is removed in vacuo to a dryness and the residue partitioned between ethylacetate and water. The organic layer is washed with water, aqueous NaHCO$_3$, and then dried over MgSO$_4$. After evaporation of the solvent, the residue is chromatographed on preparative TLC using CHCl$_3$/acetone (19:1) as developing solvents. The appropriate zone is isolated and extracted with CHCl$_3$-acetone and the solvents are removed in vacuo to give 120 mg of product. TLC=(Silica gel-chloroform/acetone=9:1 Rf.=0.69).

Preparation of Labeled BZDs

The availability of the compounds of the present invention allows the preparation of labeled molecules thereof by standard labeling techniques well known in the art. Such labeled compounds may include radioactive or fluorescent molecules and the like, which can be used for localizing, detecting and/or measuring the pBZDr activity in cells or tissues by standard autoradiographic, histocytologic or immuno-histologic techniques and the like.

To illustrate, BZDs labeled with radioactive isotopes for use in diagnostic (imaging) or other marker assays are prepared by substituting the compound at one or more of $X_1$–$X_7$ and $R_3$–$R_{10}$ with iodine 123, 125 or 131; 3H; $^{18}$F, or $^{11}$C; the latter is preferred if a short half-life isotope for PET imaging of brain function is needed, and is preferably isolated at position 1.

Receptor Preparation

Crude membranes were prepared by homogenization of a rat forebrain sample in 20 ml of ice-cold 50 mM phosphate buffer (81 mM $Na^+$, 9 mM $K^+$) buffer with a Brinkman Polytron (setting 6, 15 sec). Buffer was added to obtain a final volume of 40 ml, and the homogenate was centrifuged in a Sorval SS-34 rotor at 39,000 g for 10 min at 0°–4° C. The resulting supernatant was decanted and discarded. The pellet was rehomogenized in ice-cold buffer, diluted, and centrifuged as before. The final pellet was resuspended in the assay buffer and held on ice for the receptor binding assay.

Receptor Binding Assay

For the receptor binding assay, aliquots of the membrane preparation were incubated for 90 min at 4° C. in 50 mM phosphate buffer containing 0.5 nM [$^3$H]RO-4864 and various concentrations of the unlabeled test compounds. The assay was terminated by rapid filtration through Whatman GF/B filters under vacuum. The filters were washed three times with 5-ml aliquots of ice-cold buffer, and the bound radioactivity trapped on the filters was counted by liquid scintillation spectrometry. All assays were done in duplicate and specific binding was defined as the total [$^3$H]RO5-4864 bound minus that bound in the presence of 1000 nM RO5-4864.

Cell Culture

The rat pancreatic tumor cell line (AR42J) was obtained from the American Type Culture Collection. The human colon adenocarcinoma (HT-29) and mouse melanoma (B16 F10) were obtained from the in-house tumor bank. The HT-29 cell line is used to generate the CX-1 tumor in nude mice. All cell lines were propagated in Dulbecco's modified Eagle's medium (DMEM) supplemented with 10% fetal bovine serum (FBS) and incubated in a humidified atmosphere of 90% air/ 10% $CO_2$ at 37° C. These cell lines were maintained at Biomeasure, Inc. and were free of mycoplasma as judged by the indirect (Hoechst) method and the direct (Agar) method.

Proliferation Assay

Growth Curves—The AR42J and HT-29 cells were plated at $5 \times 10^4$ cells per well and the B16 F10 was plated at $1 \times 10^4$ cells per well in 24 well tissue cult ure dishes in 1ml of DMEM supplemented with 10% FBS. Peptides, diluted in tissue culture medium, were added on Day 0 only to duplicate wells at the concentrations indicated in Table 1. Trial experiments indicated that doses of peptide given more than one time or on Day 1 did not increase inhibition of cell growth of the AR42J cells. The tissue culture plates were incubated at 37° C. in a humidified atomsphere of 90% air/10% $CO_2$ for up to 8 days. At various times, single cell suspensions were obtained by washing the wells with DMEM, adding 0.5 ml of 0.05% trypsin—0.53 mM EDTA, incubating at 37° C. for 5 min., triturating, and adding 0.5ml of DMEM supplemented with 10% FBS to inhibit the trypsin. The total content of each well was added to Isoton and counted using a Coulter Counter model ZF attached to a Channelizer model 256 to ensure that a uniform single cell population was obtained.

Data Analysis

The inhibition constants (Ki) were calculated from the equation $Ki = IC50/(I + L/Kd)$, where L is the radioligand concentration and Kd is the equilibrium dissociation constant for the radioligand. The IC50 was derived from the inhibition data by linear least squares regression of log (B/Bt-B) versus log I, where I is the test compound concentration, Bt is the total amount of radioligand specifically bound, and B is the amount of specific binding in the presence of a given concentration of the unlabeled test compound. The IC50 is the antilog of log I, when the expression log (B/Bt-B) equals zero.

RESULTS

The relative binding affinities of various compounds having formulae within formulae I or II to the central and peripheral BZD receptors are shown in Table I. Prior art compounds R05-4864, diazepam, and clonazepam are also listed in Table 1. A small number in the "peripheral BZD" column and a large number in the "neural BZD" column indicates preferential binding to peripheral BZD.

Table 2 shows the effect of the peripheral benzodiazepine BIM-I8154 on the proliferation of tumor cells in vitro. It was found that BIM-18154 did not inhibit the growth of AR42J cells, and was marginally active at 100 nM in inhibiting the growth of Bl6 F10 cells. In contrast to the results using AR42J and B16 F10 cells, BIM-18154 was active in inhibiting the growth of HT-29 cells; there was approximately a 35% inhibition of growth on day 4. These experiments were performed using a single application of test sample; a more profound effect on cell growth may be detected by multiple applications. Although the mechanism of action for BIM-18154 is unknown, these results indicate that BIM-18154 or other peripheral benzodiazepines of the invention may be useful for treating certain forms of cancer, particularly colon cancers, leukemia, and melanoma/thymoma. Table 3 lists those tumors wherein pBZD receptors are expressed and Table 4 shows the binding of the prior art peripheral benzodiazepine R05-4864 to tumors (receptor concentration). These tumors thus are targets for anti-proliferative therapy with the pBZDs of the invention.

A composition in accordance with the present invention comprises an effective amount of the compounds of the invention to inhibit cell growth or proliferation and a pharmaceutically acceptable carrier.

A method of treating cancer comprises administering an effective amount of the compound of the invention, in a single or multiple dosage, to a subject afflicted with cancer to inhibit growth or proliferation of said cancer. Similarly, a condition arising from abnormal activity of the peripheral BZD receptor (pBZDr) could be treated with the compounds of the invention. (See Table 3).

The compounds of the invention being differentially selective for pBZD receptors, these compounds could also be used as carriers of cytotoxic agents by linking (conjugating) the pBZds with any suitable cytotoxic agents by any standard techniques well known to one of ordinary skill in the art. Some examples of such cytotoxic agents are α-emitting radioisotopes, ricin or diphtheria toxins and the like.

It is understood that the examples and embodiments described herein are for illustrative purposes only and that various modifications or changes in light thereof will be suggested to persons skilled in the art and are to be included within the spirit and purview of this application and scope of the appended claims.

TABLE 1
BENZODIAZEPINE RECEPTOR BINDING - (nM)

| COMPOUND NUMBER | PERIPHERAL BZD | NEURAL BZD |
|---|---|---|
| RO5-4864 | 0.59 | 7208 |
| BIM-18154 | 0.68 | 10000 |
| BIM-18156 | 1.68 | 10000 |
| DIAZEPAM | 23 | 8.4 |
| CLONAZEPAM | 10000 | 0.55 |
| BIM-18272 | 3.1 | 10000 |
| BIM-18268 | 12 | 10000 |
| BIM-18269 | 53 | 10000 |

TABLE 2
The Effect of the Benzodiazepine, BIM-18154, on the Proliferation of Tumor Cells in vitro.

| Cell Line | | nM | Day 2 | Day 3 | Day 4 | Day 5 |
|---|---|---|---|---|---|---|
| Pancreas | AR42J | 1 | | 90.6 | | 86.4 |
| | | 10 | | 92.1 | | 90.0 |
| Melanoma | B16 F10 | 1 | 92.7 ± 10.8 | 91.0 ± 5.3 | 95.4 ± 2.5 | |
| | | 10 | 95.5 ± 5.3 | 85.0 ± 5.6 | 95.2 ± 4.3 | |
| | | 100 | 101.9 | 86.8 | 84.4 | |
| Colon | HT-29 | 1 | | 118 | 73.6 ± 2.2 | 104 |
| | | 10 | | 117 | 66.5 ± 5.3 | 90.8 |

Values = mean ± sem; n ≧ 3.

TABLE 3
TUMORS POSITIVE FOR PERIPHERAL BENZODIAZEPINE RECEPTORS

Small Cell Lung Carcinoma H69
B16 Melanoma
MT/W9A Breast Tumor
MCF-7 Breast Tumor
AT3 Prostate
P338 Leukemia
Swarm Chondrosarcoma
Small Cell Lung Carcinoma LX-1
Neuroblastoma Nle-115
HL-60 Leukemia

TABLE 4
PERIPHERAL BENZODIAZEPINE BINDING TO TUMORS

| Tumor | | Receptor Concentration (fmoVmg Protein) |
|---|---|---|
| MCF-7 Breast (human) | [$^3$H]RO5-4864 | 3240 ± 506 |
| B16 Melanoma (murine) | [$^3$H]RO5-4864 | 2729 ± 524 |
| LX-1 Small Cell Lung (human) | [$^3$H]RO5-4864 | 2627 ± 480 |
| CA 20948 Pancreas (murine) | [$^3$H]RO5-4864 | 642 ± 160 |
| Swarm Chondrosarcoma (murine) | [$^3$H]RO5-4864 | 24590 ± 3065 |
| AT-3 Prostate (murine) | [$^3$H]RO5-4864 | 9899 ± 946 |
| HL-60 Leukemia (human) | [$^3$H]RO5-4864 | 243288 ± 16089 |
| P388 Leukemia (murine) | [$^3$H]RO5-4864 | 2832 ± 1168 |
| MTW9A Breast (murine) | [$^3$H]RO5-4864 | 7144 ± 2292 |

TABLE 4-continued
PERIPHERAL BENZODIAZEPINE BINDING TO TUMORS

| Tumor | | Receptor Concentration (fmoVmg Protein) |
|---|---|---|
| H-69 Small Cell Lung (human) | [$^3$H]RO5-4864 | 2.14 |

What is claimed is:

1. A compound of the formula I:

wherein each X, $X_1$, $X_2$, $X_3$, $X_4$, $X_5$, $X_6$, and $X_7$, independently, is hydrogen, halogen (F, Cl, Br, I), $C_1$-$C_4$ straight or branched alkyl, $C_1$-$C_4$ alkoxy, $C_1$-$C_4$ alkylthio, hydroxy, nitro, cyano, amino, or trifluoromethyl; $R_1$=H, $C_1$-$C_4$ alkyl, cyclo $C_3$-$C_5$alkyl, $C_1$-$C_4$ alkenyl, $CH_2$-$CO_2H$, or $CH_3$-C=O; $R_2$=a member of the group of the formula (Ia)

wherein each $R_3$, $R_4$, $R_7$, $R_8$, $R_9$, and $R_{10}$, independently, can be any of the groups listed as possibilities for $X_1$–$X_7$, and can be attached at any available ring carbon atom, said $R_2$ group being bonded to $(CH_2)$ in via any available ring carbon atom; $n=0$ or $1$; and $m=$ an integer between 0 and 4 provided that m is at least 1 when $n=0$.

2. A compound of formula II:

wherein X=each $X_1$, $X_2$, $X_3$, $X_4$, $X_5$, $X_6$ and $X_7$, independently, is hydrogen, halogen (F, Cl, Br, I), $C_1$–$C_4$ straight or branched alkyl, $C_1$–$C_4$ alkoxy, $C_1$–$C_4$ alkylthio, hydroxy, nitro, cyano, amino or trifluoromethyl; $R_1=H$, $C_1$–$C_4$ alkyl, cyclo $C_3$–$C_5$ alkyl, $C_1$–$C_4$ alkenyl, $CH_2$–$Co_2H$, or $CH_3$–$C=O$; $R_2$ a member of the group of the formula (Ia)

wherein $R^1$, $R^2$, and $X_1$, $X_7$ are defined the same as in formula (I).

3. The compound of claim 1, wherein $R_1$ is methyl, $X_1$–$X_7$ are hydrogen, $R_2$ is phenyl or substituted phenyl, and n and m are zero.

4. The compound of claim 1, being 1,3-dihydro-5-phenyl-3-(4-fluorobenzoyl)-1-methyl-2H-1,3,4-benzotriazepin2-one.

5. The compound of claim 1, being 1,3-dihydro-5-phenyl-3-(3,4-dichlorobenzoyl)-1-methyl-2H-1,3,4-benzotriazepin-2-one.

6. The compound of claim 1, being 3-dihydro-5-phenyl-3-(4-chlorobenzoyl)-1-methyl-2H-,3,4-benzotriazepin2-one.

7. The compound of claim 1, being 1,3 dihydro-5-phenyl-3-(3,4-difluorobenzoyl)-1-methyl-2H-1,3,4-benzotiazepin-2-one.

8. The compound of claim 2, wherein $R_1$ is methyl, $X_1$–$X_8$ are hydrogen, and $R_2$ is phenyl or substituted phenyl.

9. The compound of claim 2, being 1,3-dihydro-5-phenyl-3-(4-fluorophenyl)-methyl-i-methyl-2H-1,3,4-benzotriazepin-2-one.

10. The compound of claim 2, being 1,3-dihydro-5-phenyl-3-(3,4-dichlorophenyl)-methyl-l-methyl-2H-1,3,4benzotriazepin-2-one.

11. The compound of claim 2, being 1,3-dihydro-5-phenyl-3-(4-chlorophenyl)-methyl-i-methyl-2H,3,4-benzotriazepin-2-one.

12. A composition comprising an amount of the compound of claim 1 effective to inhibit cell growth and proliferation, and a pharmaceutically acceptable carrier 13. A composition comprising an effective amount of the compound of claim 2 effective to inhibit cell growth and proliferation, and a pharmaceutically acceptable carrier.

14. A therapeutic method comprising administering an effective amount of the composition of claim 12 to a subject having a disorder resulting from an abnormal level of peripheral benzodiazepine receptor activity, to treat said disorder.

15. A therapeutic method comprising administering an effective amount of the composition of claim 13 to a subject having a disorder resulting from an abnormal level of peripheral benzodiazepine receptor activity, to treat said disorder.

16. A method for detecting peripheral benzodiazepine receptor (pBZDr) activity in a cell or tissue, comprising contacting said cell or tissue with a labeled compound of claim 1 or claim 2 and detecting the presence of said labeled compound in said cell or tissue.

17. The compound of claim 1 labeled with a radioactive isotope.

18. The compound of claim 2 labeled with a radioactive isotope.

19. The compound of claim 1 conjugated with a cytotoxic agent.

20. The compound of claim 2 conjugated with a cytotoxic agent.

* * * * *

UNITED STATES PATENT AND TRADEMARK OFFICE
CERTIFICATE OF CORRECTION

PATENT NO. : 5,091,381

DATED : February 25, 1992

INVENTOR(S) : Sun H. Kim and John E. Taylor

It is certified that error appears in the above-identified patent and that said Letters Patent is hereby corrected as shown below:

Column 1, line 25, correct the spelling of "benzodiazepines";

Column 3, line 13, correct the spelling of "sublingually";

Column 4, line 15, correct the spelling of "autoimmune";

Column 4, line 16, correct the spelling of "arthritis";

Column 4, line 17, correct the spelling of "lymphokine";

Column 5, line 31, change "3S6" to --386--;

Column 5, line 32, change "(JP 45,01, 1,148)" to --(JP 45,011,148);

Column 5, line 48, change "2H-,3,4-benzotriaze-" to --2H-1,3,4-benzotriazepine";

Column 5, line 50, delete "oine"

Column 6, line 30, change "DMP" to --DMF--;

Column 6, lines 41-42, correct the heading so it reads as follows:   --3-(4-Fluorophenyl)methyl-1-methyl-2H-1,3,4-benzotriazepine-2-one--;

Column 6, line 49, correct the spelling of "fluorobenzyl";

Column 8, line 31, change "BIM-I8I54" to --BIM-18154--;

UNITED STATES PATENT AND TRADEMARK OFFICE
CERTIFICATE OF CORRECTION

PATENT NO. : 5,091,381

DATED : February 25, 1992

INVENTOR(S) : Sun H. Kim and John E. Taylor

It is certified that error appears in the above-identified patent and that said Letters Patent is hereby corrected as shown below:

Column 11, claim 1, line 4, after "$X_1-X_7$", delete the period;

Column 12, claim 6, line 20, after "being", insert --1, --;

Column 12, claim 7, line 24, correct the spelling of "benzodiazepin";

Column 12, claim 9, line 30, "methyl-i-methyl" should read as follows: --methyl-1-methyl--;

Column 12, claim 11, line 36, "methyl-i-methyl" should read as follows: --methyl-1-methyl--.

Signed and Sealed this

First Day of June, 1993

Attest:

MICHAEL K. KIRK

*Attesting Officer*  *Acting Commissioner of Patents and Trademarks*